(12) United States Patent
Blankenstein et al.

(10) Patent No.: US 10,585,021 B2
(45) Date of Patent: Mar. 10, 2020

(54) DUAL CHAMBER REAGENT MIXING CONTAINER

(71) Applicant: Instrumentation Laboratory Company, Bedford, MA (US)

(72) Inventors: Gert Blankenstein, Dortmund (DE); Hansong Zeng, Lowell, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 738 days.

(21) Appl. No.: 15/234,138

(22) Filed: Aug. 11, 2016

(65) Prior Publication Data

US 2018/0045627 A1    Feb. 15, 2018

(51) Int. Cl.
*B01F 13/00* (2006.01)
*G01N 1/38* (2006.01)
(Continued)

(52) U.S. Cl.
CPC ............ *G01N 1/38* (2013.01); *B01F 13/0022* (2013.01); *B01F 13/0818* (2013.01); *B01F 15/0215* (2013.01); *B01F 15/0225* (2013.01); *B01F 15/0237* (2013.01); *B01L 3/52* (2013.01); *B65D 51/002* (2013.01); *B65D 81/3255* (2013.01); *G01N 35/10* (2013.01); *G01N 35/1002* (2013.01); *B01F 2215/0037* (2013.01); *B01L 3/523* (2013.01); *B01L 2200/16* (2013.01); *B01L 2300/044* (2013.01); *B01L 2300/047* (2013.01); *B01L 2300/0861* (2013.01);
(Continued)

(58) Field of Classification Search
CPC ............... B01F 13/022; B01F 15/0215; B01F 13/0022; B01F 13/0818; B01F 15/0225; B01F 15/0237; B01F 2215/0037; G01N 1/38; G01N 35/10; G01N 35/1002; G01N 2001/386; G01N 2035/00534; G01N 2035/1058; B01L 3/52; B01L 3/523; B01L 2200/16; B01L 2300/044; B01L 2300/047; B01L 2300/0861; B01L 2300/123; B01L 2400/0478; B01L 2400/06; B01L 2400/0683; B65D 51/002; B65D 81/3255
See application file for complete search history.

(56) References Cited

U.S. PATENT DOCUMENTS 4,515,586 A * 5/1985 Mendenhall .......... A61J 1/2089
                                                 604/416
4,793,475 A    12/1988 Itzel
(Continued)

FOREIGN PATENT DOCUMENTS

CN    1081512 A    2/1994
CN    101896407 A    11/2010
(Continued)

OTHER PUBLICATIONS

ISR and Written Opinion, International Application No. PCT/US2017/045692 dated Oct. 16, 2017, 12 pages.
(Continued)

*Primary Examiner* — Anshu Bhatia
(74) *Attorney, Agent, or Firm* — Burns & Levinson, LLP; Joseph P. Quinn (57) ABSTRACT

Described is an automated reagent mixing container for separately storing and automatically mixing together at least two stored reagent components.

14 Claims, 7 Drawing Sheets

(51) Int. Cl.
*B65D 81/32* (2006.01)
*G01N 35/10* (2006.01)
*B01F 15/02* (2006.01)
*B01F 13/08* (2006.01)
*B01L 3/00* (2006.01)
*B65D 51/00* (2006.01)
*G01N 35/00* (2006.01)

(52) U.S. Cl.
CPC . *B01L 2300/123* (2013.01); *B01L 2400/0478* (2013.01); *B01L 2400/06* (2013.01); *B01L 2400/0683* (2013.01); *G01N 2001/386* (2013.01); *G01N 2035/00534* (2013.01); *G01N 2035/1058* (2013.01)

(56) References Cited

U.S. PATENT DOCUMENTS

| | | | |
|---|---|---|---|
| 4,898,293 | A | 2/1990 | Morel |
| 5,114,411 | A | 5/1992 | Haber et al. |
| 5,250,440 | A | 10/1993 | Kelln et al. |
| 5,525,299 | A | 6/1996 | Lowe |
| 5,578,272 | A | 11/1996 | Koch et al. |
| 6,132,400 | A | 10/2000 | Waldenburg |
| 6,527,110 | B2 | 3/2003 | Moscovitz |
| 6,533,113 | B2 | 3/2003 | Moscovitz |
| 7,017,735 | B2 | 3/2006 | Carlson |
| 9,051,099 | B2 | 6/2015 | Salinas |
| 9,102,441 | B1 | 8/2015 | Orvik |
| 2005/0187533 | A1* | 8/2005 | Filler .................. A61J 1/2096 604/403 |
| 2008/0121591 | A1 | 5/2008 | Knight et al. |
| 2009/0308831 | A1 | 12/2009 | Anderson |
| 2010/0000341 | A1 | 1/2010 | Hasegawa et al. |
| 2010/0044377 | A1 | 2/2010 | Porter |
| 2010/0089860 | A1 | 4/2010 | Wiggins et al. |
| 2012/0183956 | A1 | 7/2012 | Ross et al. |
| 2013/0331298 | A1 | 12/2013 | Rea |
| 2013/0338606 | A1* | 12/2013 | Conzone .......... A61M 5/31513 604/230 |
| 2015/0038876 | A1 | 2/2015 | Gonzalez-Zugasti et al. |
| 2015/0076170 | A1 | 3/2015 | Goettke |

FOREIGN PATENT DOCUMENTS

| | | | |
|---|---|---|---|
| EP | 2110332 A1 | 10/2009 | |
| EP | 2399564 | 12/2011 | |
| EP | 2399564 A1 * | 12/2011 | ............ A61J 1/2093 |
| EP | 2647584 A2 | 10/2013 | |
| FR | 1429002 A | 2/1966 | |
| WO | 2007/062745 | 6/2007 | |
| WO | 2007/003001 A1 | 11/2007 | |
| WO | 2009075637 A1 | 6/2009 | |
| WO | 2015/151252 A1 | 10/2015 | |
| WO | 2016/087626 | 6/2016 | |

OTHER PUBLICATIONS

International Preliminary Report on Patentability for PCT Application No. PCT/US2017/045692, dated Feb. 21, 2019.
First Office Action issued in corresponding Chinese application No. 201780049313.8, dated Sep. 18, 2019, (14 pages) and English translation thereto (20 pages).
First Examination Report issued in corresponding European application No. 17757952.1, dated Nov. 19, 2019, (8 pages).

* cited by examiner

DUAL CHAMBER REAGENT MIXING CONTAINER

TECHNICAL FIELD OF THE INVENTION

The present invention is related to the field of automated clinical diagnostics, more specifically containers for storing and mixing components of reagents used in diagnostic tests conducted in an automated clinical analyzer, methods of use, and methods of making thereof.

BACKGROUND

In many in-vitro diagnostic (IVD) testing procedures there is a need to prepare reagents by reconstituting and/or mixing multiple necessary components, some in a liquid and others in a powder format. Currently, reconstituting or mixing reagents for an IVD procedure is achieved by manual operation. For instance, in a diagnostic testing lab, before using the reagents for sample testing, typically body fluids such as whole blood, plasma, serum, urine, cerebrospinal fluid and so on, medical workers collect different reagent components from separate vials/bottles, use a pipette to pipette diluents with a certain volume to a vial of powder reagents or to a vial with concentrated liquid reagents, wait for certain time for reconstitution, and finally mix the reagents manually by shaking, stirring, or rotating, for example. This manual process reduces the speed in which a diagnostic test takes place, increases the risk of human error and operator contamination with potentially toxic chemicals, and raises the cost of packaging.

Dual-chamber syringe systems developed for drug preparation, provide a solution for mixing drug components such as a lyophilized active component and a diluent like water or saline, by packaging two drug components in a single device such as a dual barrel syringe thereby partially automating the drug reconstitution process. However, the syringe device is disadvantaged by a complex manufacturing and assembly process. The cost of the manufacturing and assembly is not a factor for drug manufacturers in view of the price of the drug to the consumer. But such devices are not practical for IVD test applications, where the packaging cost for IVD test applications must be controlled to be very low because of the low cost of the test to the consumer.

In addition, the volume inside a syringe is relatively low, compared to reagent volume in IVD testing, potentially a liter or more, such as a test run by an automated clinical analyzer, to achieve effective reconstitution and mixing. In addition to the need to reconstitute reagents for IVD applications, the contents of current reagent vials used in diagnostic instruments such as automated clinical analyzers, are subject to evaporation when on-board the instrument. Such evaporation compromises reagent stability, alters reagent concentration, and is generally wasteful of reagents, increasing the cost for the user.

In order to improve the current reagent preparation process and usage efficiency for IVD applications in a clinical analyzer, a reagent packaging solution with multi-components storage, automated reconstitution and mixing, and evaporation prevention is needed.

SUMMARY OF THE INVENTION

The present invention relates to the field of clinical diagnosis, diagnostic assays in particular, and more specifically containers and methods for storing and automated mixing of reagent components for use in a diagnostic assay in an automated clinical analyzer.

In one aspect, the invention described herein is related to a reagent mixing container having two integrated chambers: a first chamber with a first open end, a second open end, and a lumen extending therebetween, a supplemental chamber having a first open end, a second open end, and a lumen therebetween, and a stopper positioned between the second end of the first chamber and the second end of the supplemental chamber. In one embodiment, the stopper is elastomeric, self-lubricating, encloses a magnetic bar or one or more magnetic particles, or is a one way-valve.

The stopper has two positions: a first position and a second position. The stopper is sealingly positioned between the second end of the first chamber and the second end of the supplemental chamber in the first position. In this position, the stopper seals the contents of the first chamber from the contents of the supplemental chamber. For example, the circumference of the stopper contacts the inner wall of the container to prevent leakage of contents between the first and supplemental chamber in the first position. The stopper is in the second position after the stopper is displaced or compromised such that the stopper no longer seals the first chamber from the contents of the second chamber. For example, in the second position, the stopper is displaced, i.e., unseated such that the circumference of the stopper is no longer in contact with the inner wall of the container. In another embodiment of the stopper, e.g., a one-way valve, the stopper is compromised when the valve opens to permit the contents of the first chamber and the contents of the supplemental chamber to come in contact with one another.

In the second position of the stopper, the lumen of the supplemental chamber is co-extensive and in fluid communication with the lumen of the first chamber.

In one embodiment, the reagent mixing container further includes a perforatable, self-sealing cap positioned at the first open end of the first chamber, a plunger sealingly positioned at the first open end of the supplemental chamber and slideably moveable in the lumen of the supplemental chamber from the supplemental chamber first end towards the supplemental chamber second end.

The reagent mixing container contains a lyophilized component of a reagent and/or a liquid component of a reagent in at least one of the first chamber and the supplemental chamber. In one embodiment, for example, the lyophilized reagent is a lyophilized PT (prothrombin time) reagent, lyophilized Thrombin Time reagent, or lyophilized bovine thrombin reagent. Alternatively, the liquid reagent is deionized water, a buffer, or concentrated reagents such as but not limited to concentrated PT (prothrombin time) reagent, alternatively, a concentrated D-Dimer reagent, or latex reagent.

In another aspect, the invention described herein is related to a system for automated mixing of reagents. The system includes the features of the dual chamber reagent mixing container described above. Also included in the system is a clinical analyzer in one embodiment having an actuator for driving the plunger into the lumen of the supplemental chamber, a stepper motor for driving the actuator, an electromagnetic coil (or magnet) for driving rotation of the reagent mixing container or actuating movement of the magnetic mixing bar or the magnetic beads.

In another aspect, the invention described herein is related to a method for automated reagent mixing. The method comprises a number of steps. In one embodiment of the method, the dual chamber reagent mixing vial comprising a first reagent component in the first chamber and a second reagent component in the supplemental chamber is provided in the mixing system described above. The plunger is transferred from a non-activated position where it is positioned in the first end of the supplemental chamber to seal the opening at the first end, to an activated position by advancing the plunger automatically in the lumen of the supplemental chamber towards the second end of the supplemental chamber. By advancing the plunger towards the second end of the supplemental chamber, the contents of the supplemental chamber, liquid, powder or gas, is compressed against the stopper 16. In one embodiment, the stopper is displaced by compression of the contents of the supplemental chamber against the stopper to unseat the stopper. Alternatively, compression of the contents of the supplemental chamber against the one-way valve stopper compromises the stopper by opening the stopper. Following unseating of the stopper, or opening of the one-way valve stopper, the lumen of the first chamber and the lumen of the supplemental chamber are in fluid communication.

In one embodiment of this aspect of the invention, after the stopper is displaced or compromised, the first reagent and the second reagent components are mixed together by actuating a rotor to rotate the reagent mixing container. In an alternative embodiment, the components of the reagents are mixed by rotation of the stopper encasing a magnetic bar or by rotation of at least one magnetic particle.

In yet another aspect, the invention described herein is related to a method for introducing reagent components into the dual chamber reagent mixing container described above. The reagent container described above is readied with the perforatable sealing cap unsealed and the plunger in its sealing position in the opening at the first end of the supplemental chamber. A liquid form of the second component is lyophilized in the lumen of the supplemental chamber while the sealing cap remains unsealed. The stopper is securely positioned at the interface of the second end of the first chamber and the second end of the second chamber to seal the contents of the lumen of the first and second chambers from each other. A liquid is introduced into the lumen of the first chamber and the sealing cap is pushed into the opening at the first end of the first chamber to form a seal whereby the reagent mixing container is rendered air tight.

DESCRIPTION OF THE INVENTION

Described below is an automated dual chamber reagent mixing container for separately storing and automatically mixing together at least two stored reagents, methods for mixing stored reagents, and methods for manufacturing the dual chamber reagent mixing container with its content for use in an automated clinical analyzer, including hemostasis analyzers, immunoassay analyzers, and chemistry analyzers, to name a few. Various combinations and arrangements of reagents and chambers are contemplated by the invention.

These and other objects, along with advantages and features of the present invention described herein, will become apparent through references to the following description and the claims. Furthermore, it is to be understood that the features of the various embodiments described herein are not mutually exclusive and can exist in various combinations and permutations.

In one aspect, the invention is directed to a device for storage of and automated mixing of two reagents for use in an automated clinical analyzer, for example, Hemostasis Analyzer, ACLTOP® 300, 500 and 700 series, (Instrumentation Laboratory® Company, Bedford, Mass.).

Figure 1:
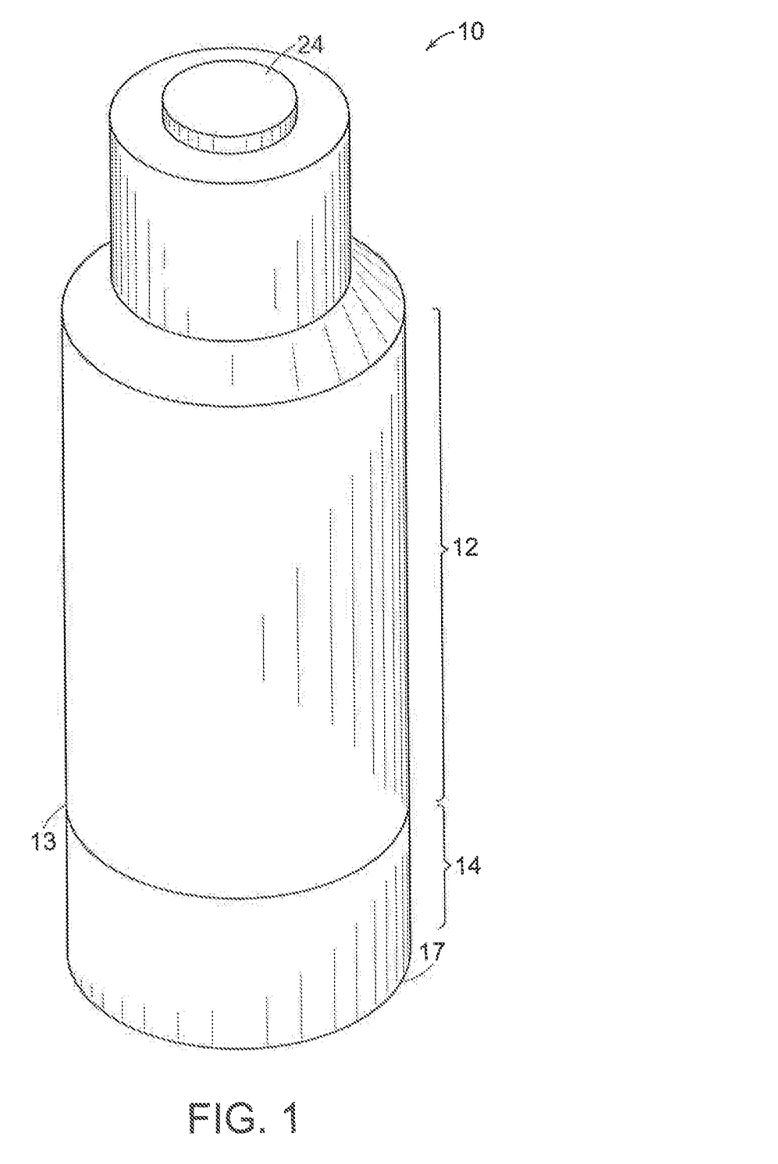
FIG. 1 illustrates a perspective view of the reagent mixing container according to an embodiment of the invention.
Figure 2A:
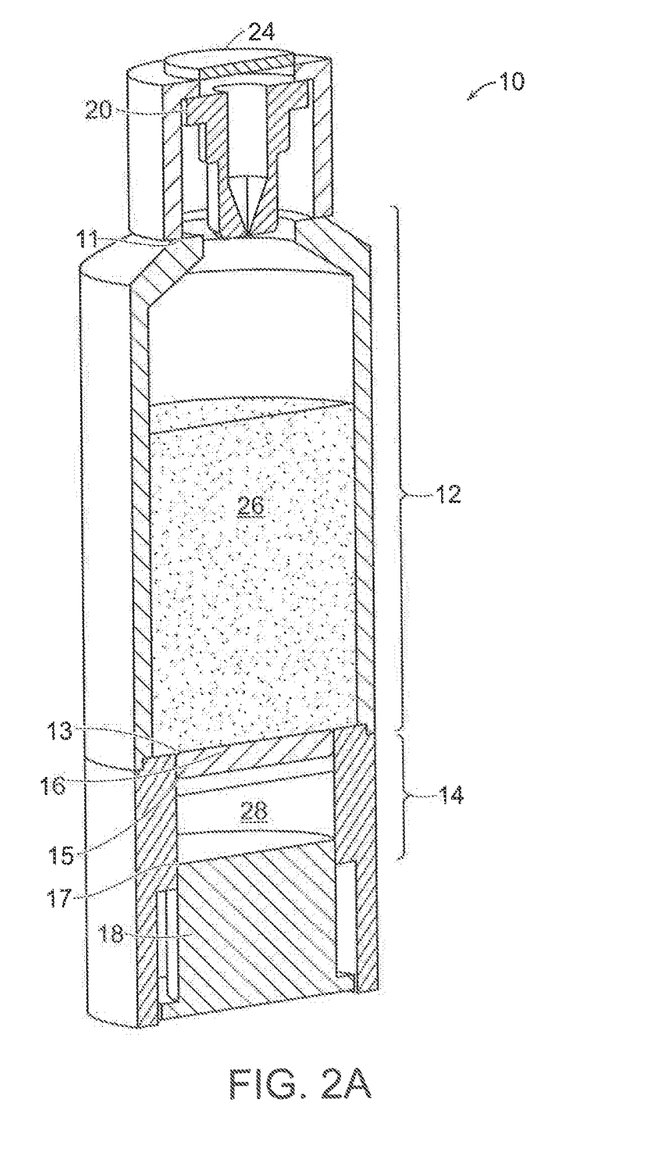
FIG. 2A illustrates a transverse section of the reagent mixing container illustrated in FIG. 1.

Referring to FIGS. 1 and 2A, a reagent mixing container 10 according to the invention includes a first chamber 12, a supplemental chamber 14, a stopper 16, a plunger 18, a resealable cap 20, and, optionally, a protective cap 24. The first chamber 12 has a first end 11 positioned on the top of the container 10, a second end 13 opposite the first end 11 positioned along the long axis of the container 10 below the first end 11, and a lumen 26 extending between the first end 11 and the second end 13 of the first chamber 12. The volume of the first chamber may be in the range of about 10 ml to 5,000 ml, 10 ml to 1000 ml, 10 ml to 500 ml, 10 ml to 100 ml, 100 ml to 500 ml, 100 ml to 250 ml, or 100 ml.

The supplemental chamber 14 has a second end 15 positioned adjacent the second end 13 of the first chamber 12, a first end 17 opposite the second end 15, and a lumen 28 extending between the first end 17 and the second end 15 of the supplemental chamber 14. The volume of the supplemental chamber 14 may be about 0.1 ml to 100 ml. Each of the first chamber 12 and the supplemental chamber 14 may enclose one or more liquid or dry reagents.

With continued reference to FIG. 1, the plunger 18, has two positions: a sealing or first position in which the plunger 18 seals the first end 17 of the supplemental chamber 14 (shown in FIG. 1) forming a lumen 28 in the supplemental chamber 14, and an actuated or second position in which the plunger 18 is actuated by an external force, described in greater detail below with respect to FIG. 2B and illustrated in FIGS. 5A-5C, to move the plunger in the lumen 28 from the first end 17 towards the second end 15 of the supplemental chamber 14 as indicated by the arrow in FIG. 2B. When the plunger 18 is moved as indicated by arrow, the stopper 16 is displaced from circumferential contact with the inner wall 11 of the container 10.

The resealable cap 20 is positioned at an opening of the first end or top 11 of the first chamber 12 and is perforatable when a probe, such as a pipette or needle (not shown) pierces the cap 20. The cap 20 reseals when the probe is withdrawn. When the reagent mixing container 10 is not in use, the cap 20 is closed to seal the first chamber 12 from room air thereby preventing evaporation of contents within the chambers of the reagent mixing container 10.

Figure 2B:
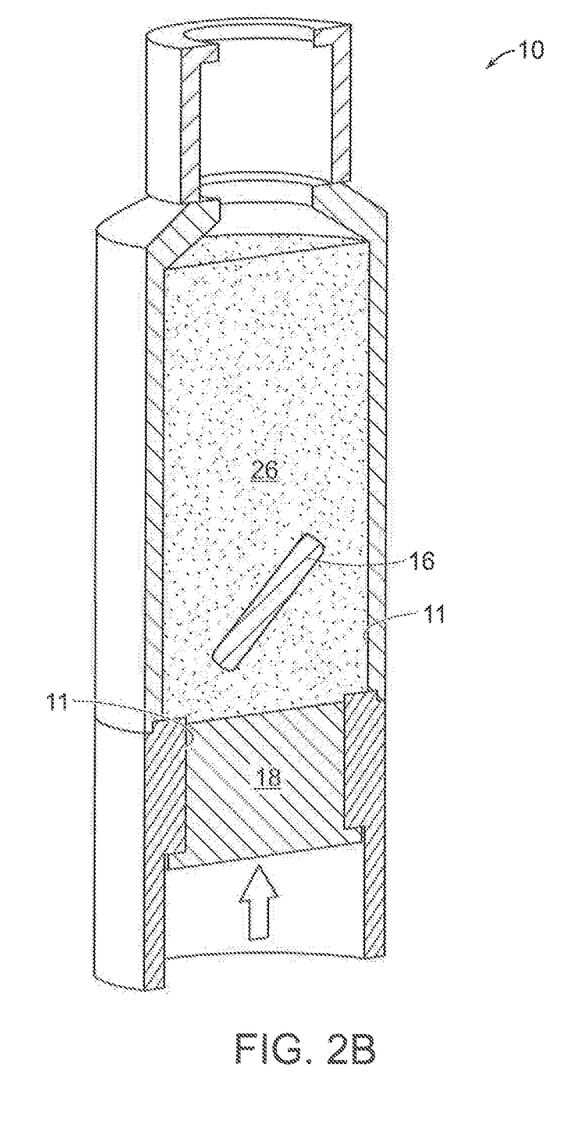
FIG. 2B illustrates a transverse section of the reagent container illustrated in FIG. 2A with the plunger activated to displace the stopper into a second position thereby releasing the contents of the supplemental chamber into the first chamber.

Referring to FIG. 2B, the reagent mixing container 10 has a stopper 16, positioned at the interface between the second end 13 of the first chamber 12 and the second end 15 of the supplemental chamber 14 separating the contents, such as a reagent component of the first chamber 12 (represented by stippling) from the contents, such as another reagent component, of the supplemental chamber 14. The stopper 16 is secured in position in contact with the inner wall 11 of the container 10 and seals the lumen 26 of the first chamber 12 from the contents of the lumen 28 of the supplemental chamber 14 while the reagent mixing container 10 is stored until the stopper 16 is compromised or displaced. The stopper 16 is displaced or compromised by displacing the stopper from contact with the inner wall 11 or the stopper 16 is opened (compromised) by opening a one-way valve stopper positioned between the first and supplemental chambers. By displacement, the stopper 16 is freed from its seated position against the inner wall of the container 10 and is able to freely move within the container lumen.

When the stopper 16 is displaced or the stopper 16 comprises a one way valve that is opened, the lumen 28 of the supplemental chamber 14, and the lumen 26 of the first chamber 12, are co-extensive and in fluid communication.

In various embodiments of the invention, the stopper 16 is elastomeric, for example, rubber, or plastic, and/or coated with a self-lubricating material such as Teflon® (polytetrafluoroethylene). In one embodiment of the invention, the stopper 16 is a compressible material, such as rubber or plastic, or a self-lubricating coated material 23 any one of which encloses a rotatable magnetic bar 22, illustrated in FIG. 3 or, alternatively encloses one or more magnetic particles (not shown). In one embodiment of the invention, the stopper 16 is a one way valve described below with reference to FIGS. 4A-4B.

In an embodiment of the invention, discussed in greater detail with respect to FIGS. 5A-5C below, the stopper 16 has a first position and a second position. In a first position the stopper 16 is removably positioned at the interface between the second end 13 of the first chamber 12 and the second end 15 of the supplemental chamber 14 with the circumference of the stopper 16 in contact with the inner wall 11 of the container 10. In this position, the stopper 16 seals the reagent contents of the first chamber 12 from the reagent contents of the supplemental chamber 14 as long as the stopper 16 remains undisrupted and the integrity of the stopper 16 is uncompromised. In this embodiment, while the stopper 16 is in the first position, the contents in each of the two chambers of the reagent container 10 remain separated and can be stored in this way for periods of time extending to days, weeks, months or even one or more years, prior to use without evaporation or loss of reagent activity.

Figure 3:
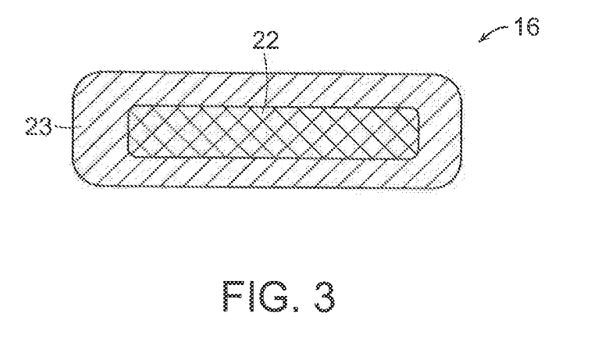
FIG. 3 illustrates a transverse section of a magnetic bar/stopper combination according to an embodiment of the invention.

As illustrated in FIG. 3, in one embodiment of the invention the stopper 16 encases a magnetic bar 22 by a material such as but not limited to rubber, a polymer such as plastic, or Teflon®. The stopper 16 is releasably secured at the interface of the lumen 26 at the second end 13 of the first chamber 12 and the lumen 28 at the second end 15 of the second chamber 14. In this embodiment, the stopper 16 is secured by compression of the stopper 16 against the interior surface of the walls of the container 10. In one embodiment, the stopper 16 has a diameter slightly larger than the diameter of the aforementioned interface so that it is secured by friction but releasable into the lumen of the container. When a force is applied to the stopper, for example, during compression of the contents of the supplemental chamber or when its integrity is compromised (such as opening a one-way valve) the stopper moves to a second position which permits the contents of the first chamber to reach the contents of the supplemental chamber.

Figure 4A:
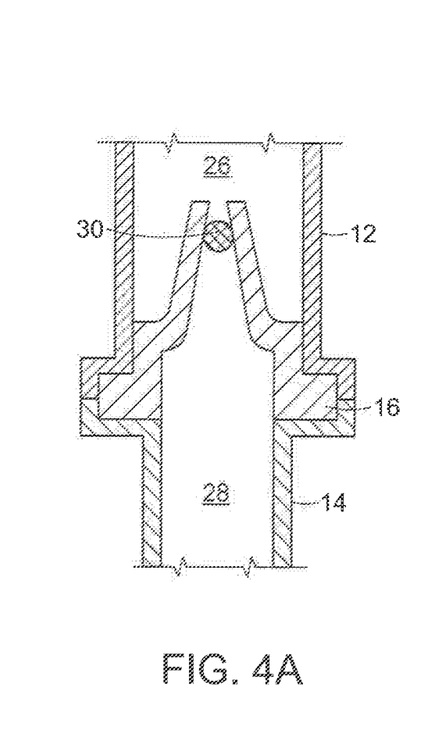
FIGS. 4A and 4B illustrate a transverse section of a one-way valve stopper according to another embodiment of the invention.
Figure 4B:
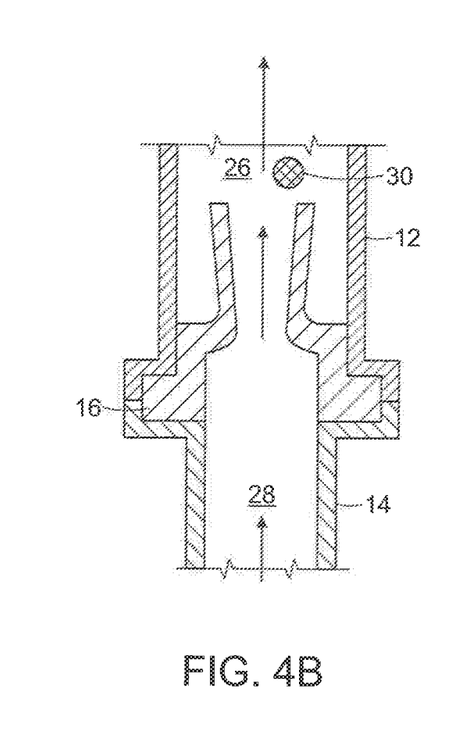

Referring to FIGS. 4A and 4B, in another embodiment of the automated reagent mixing container 10 of the invention, the stopper 16 is a one-way valve. As illustrated in FIG. 4A, the one-way valve stopper 16 in the closed (first) position prevents mixing of the contents of the lumen 26 of the first chamber 12 with the contents of the lumen 28 of the supplemental chamber 14. When positive pressure is applied by the plunger 18 while it is advanced towards the second end 15 in the lumen 28 of the supplemental chamber 14 as described below, the one-way valve 16 is compromised and opens into the lumen 26 of the first chamber 12 as illustrated in FIG. 4B. The compromised valve/stopper 16 permits the contents of the lumen 28 of the supplemental chamber 14 to reach the contents in the lumen 26 of the first chamber 12.

As illustrated in FIGS. 4A and 4B, in a particular embodiment one or more magnetic beads 30 may be positioned in the lumen 28 of the supplemental chamber 14 or positioned within the one-way valve 16. When the one-way valve/stopper is compromised and opens under pressure applied by the plunger 18 as described above, the one or more magnetic beads 30 are forced into the lumen 26 of the first chamber 12 and facilitate mixing of the components of the first chamber 12 and supplemental chamber 14 when a magnetic field is applied to the magnetic bead 30. The magnetic field may be generated by an electromagnetic coil 36 or a magnet as shown in FIG. 5C.

In another aspect, the invention is directed to a system for automated mixing of reagents in a clinical analyzer.

Figure 5A:
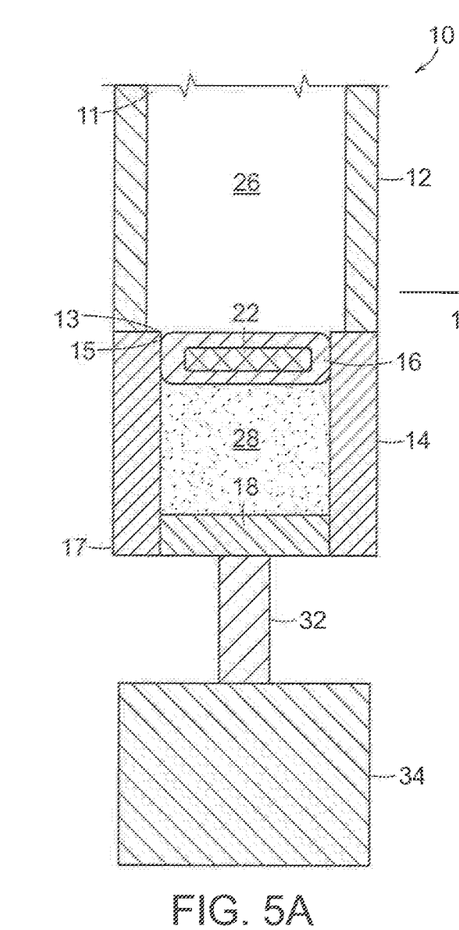
FIG. 5A illustrates a schematic view of a system for automated mixing of reagents in a clinical analyzer including the reagent mixing container shown in a non-activated transverse section, a linear actuator and a stepper motor, and an electromagnetic coil according to an embodiment of the invention.

Referring now to FIG. 5A, the system according to the invention includes the reagent mixing container 10 described above, an actuator 32, such as a linear actuator, a motor 34, such as a stepper motor, and optionally an electromagnetic coil or magnet 36 for generating a magnetic field. The actuator 32 is operably positioned to slideably advance the plunger 18 in the lumen 28 from the first end 17 of the supplemental chamber 14 towards the second end 15 of the supplemental chamber 14 up to and, optionally, slightly beyond the stopper 16 of the reagent mixing container 10.

Figure 5B:
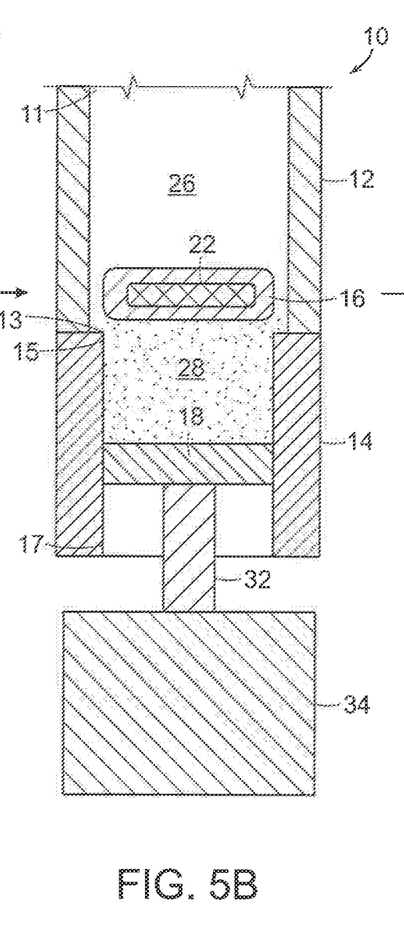
FIG. 5B illustrates a schematic view of the reagent mixing container of FIG. 5A with the plunger partially activated and the magnetic bar/stopper combination released into the lumen of the first chamber.
Figure 5C:
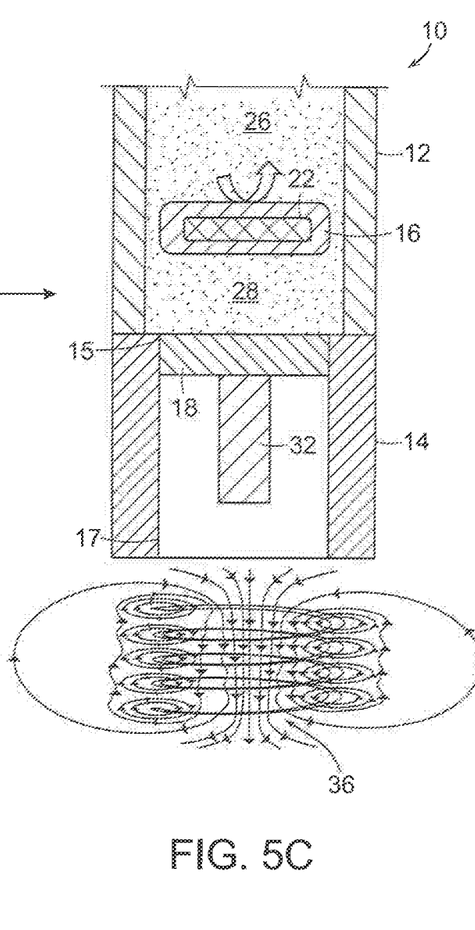
FIG. 5C illustrates a schematic view of the reagent mixing container of FIGS. 5A and 5S with the plunger fully activated, the reagent in the lumen of the second chamber moved into the lumen of the first chamber and mixed by rotating the magnetic bar/stopper combination or by rotating the reagent mixing container.

In the configuration represented by FIGS. 5B and 5C, the reagent mixing container 10 performs a mixing function. Referring to FIGS. 5B and 5C, the components, such as liquid or dry components of a reagent, in chambers 12 and 14 of the container 10, are combined when the stopper 16 is displaced, for example, by unseating the stopper 16 from its removably secured first position at the interface of the second end 13 of the first chamber 12 and the second end 15 of the second chamber 14 to the second position. In the second position, illustrated in FIG. 5B, the rubber stopper 16 is unseated and the contents of the first chamber 12 come in contact with the contents of the supplemental chamber 14.

Alternatively, as described above and illustrated in FIGS. 4A and 4B, the components in first chamber 12 contacts the components of supplemental chamber 14 when the one-way valve-stopper 16 translates from a closed to an open position. Following the opening of the valve and contact of the components of the two chambers, mixing of the components can take place.

According to one embodiment of the method of the invention, the stopper 16 is unseated or the valve-stopper 16 is opened by the action of the plunger 18 when the plunger 18 is advanced by, for example, the linear actuator 32 activated by the stepper motor 34, towards the stopper 16 in the lumen 28 of the supplemental chamber 14 from the first end 17 of the supplemental chamber 14 towards the second end. Advancing the plunger 18, as illustrated in FIGS. 5B-5C, compresses the contents of the lumen 28 of the supplemental chamber 14 whereby the compressed contents push on the stopper 16 disrupting the stopper 16 from its first position illustrated in FIG. 5A to the second position illustrated in FIGS. 5B-5C or opens the valve-stopper 16 to a second position as illustrated in FIG. 4B. The reagent component contents (liquid or powder) in the lumen 28 of the supplemental chamber 14 are advanced into the lumen 26 of the first chamber 12. Following introduction of the reagent component contents of the supplemental chamber 14 into the lumen 26 of the first chamber 12, the reagent components of the first chamber 12 contact the reagent components of the second chamber 14.

Mixing of the reagents components of the first chamber 12 with the reagents components of the second chamber 14 begins after the stopper 16 is in the second position. As discussed above, in one embodiment according to the method of the invention, the stopper encasing a magnetic stir bar 22 or alternatively one or more magnetic particles (not shown) is activated. In an embodiment of the method of the invention, the magnetic mixing bar 22 or the one or more magnetic particles is operably joined to the electromagnetic coil or a magnet 36. The electromagnetic coil 36 actuates the magnetic bar 22 or magnetic particles, illustrated in FIG. 5C, i.e., causing the magnetic bar 22 to rotate or the magnetic particles to move inside the lumen 26 of the first chamber 12 in the reagent mixing container 10, to obtain a homogeneous mixing of the reagent components of the first chamber 12 and the supplemental chamber 14.

Alternatively, the regent components of the first chamber 12 and the supplemental chamber 14 are mixed together in the first chamber 12 by rotation, such as by oscillation, of the reagent mixing container 10.

Figures 6A, 6B:
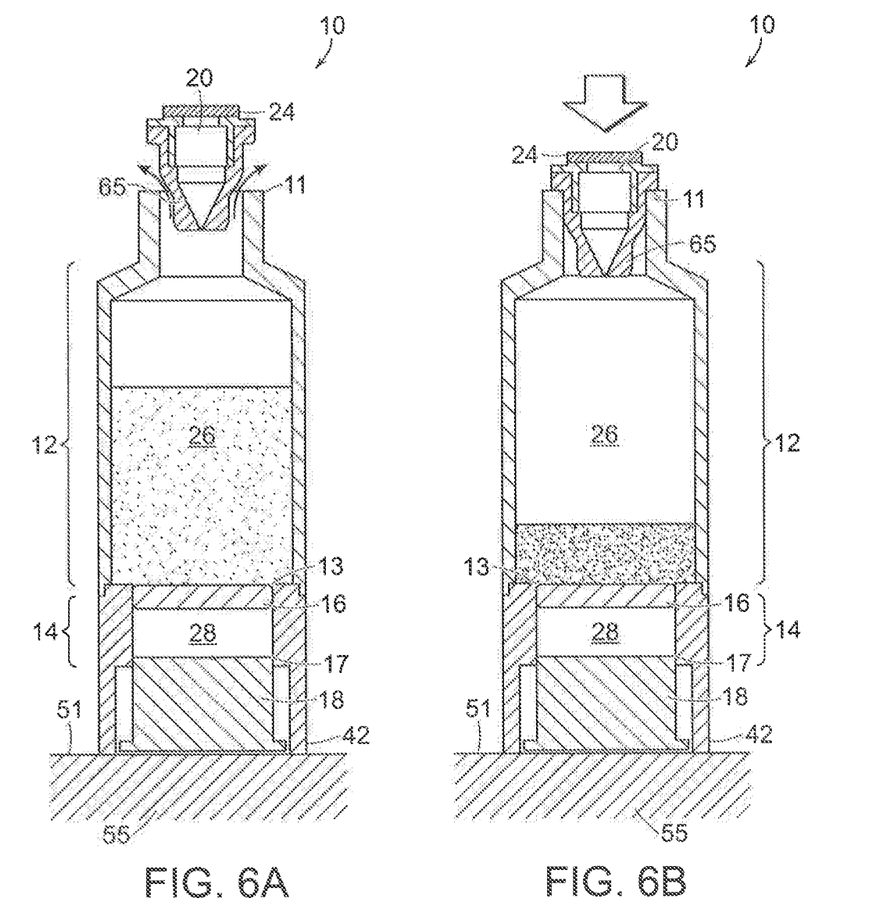
FIG. 6A illustrates a first step in preparing a lyophilized reagent in the first chamber according to one embodiment of the invention.
FIG. 6B illustrates a second step of the lyophilization procedure illustrated in FIG. 6A according to one embodiment of the invention.

In yet another aspect, the invention is directed to a method for making the reagent mixing container 10 described above. Referring to FIG. 6A, in one embodiment of the invention, a method for preparing a lyophilized reagent in the first chamber 12 is shown. In this embodiment, the plunger 18 is positioned to seal the first end 17 of the supplemental chamber 14, a diluent is added to the lumen 28 of the supplemental chamber 14, followed by securely positioning the stopper 16 at the second end 13 of the first chamber 12 to seal the lumen 28 of the supplemental chamber 14. A homogenous or a heterogeneous liquid reagent comprising two or more components is added to the lumen 26 of the first chamber 12. The liquid reagent may be, for example, a component of PT ReadiPlasTin® (Instrumentation Laboratory Company, Bedford, Mass.), a reagent used for coagulation testing. The first chamber 12 is partially filled or completely filled with the liquid reagent to the top of the lumen 26, i.e., approaching the first end 11 of the first chamber 12.

Still referring to FIG. 6A, with the liquid reagent filled to a desired level in the lumen 26 of the first chamber 12, the resealable cap 20, including a rubber septum 65, is kept in an open position. The open position, as used herein, refers to loosely placing the resealable cap 20 at the first end 11 of the chamber 12 without sealing the lumen 26 of the first chamber 12 from room air. For example, the resealable cap 20 includes a rubber septum 65 that has openings (vents indicated as arrows) at contact points between the rubber septum 65 and the opening at the first end 11 of the first chamber 12. The openings permit vacuum venting of the pre-filled liquid reagent in the lumen 26 of the first chamber 12. Vacuum venting of the liquid reagent in the lumen 26 is carried out by the application of negative pressure with the use of a pressure regulator (not shown) to control the vent-up rate. Vacuum venting proceeds until the components of the pre-filled liquid reagent in the first chamber 12 are lyophilized. The duration and pressure for vacuum venting of the liquid reagent may vary depending on the volume and/or the density of the liquid in the lumen 26.

Referring now to FIG. 6B, at the end of lyophilization, i.e., once the liquid reagent is lyophilized in the lumen 26 of the first chamber 12 to generate a lyophilized product, the resealable cap 20 is brought to a closed position from the previously open position. To bring the resealable cap 20 to the closed position, the resealable cap 20 is pushed towards the lumen 26 (as indicated by the arrow), at the first end 11 of the chamber 12 to seal the chamber 12. Sealing is achieved when the rubber septum 65 attached to the resealable cap fits securely into the opening of the upper end 11 of the lumen 26 of the first chamber 12. Sealing by the resealable cap at the first end 11 of the first chamber 12 prevents contact of the lyophilized reagents in the lumen 26 of the first chamber 12 with room air outside the dual chamber reagent mixing container 10. Sealing by the stopper at the second end 15 of the supplemental chamber 14 prevents mixing of the contents of the first chamber 12 and the supplemental chamber 14 until the stopper 16 is dislodged or its integrity compromised (e.g., the integrity of a one-way valve stopper is moved from a closed to an open valve) to permit contact between the contents of the two chambers.

Referring to FIGS. 6A and 6B, vacuum venting of the liquid reagent in the chamber 12 after lyophilization of the liquid reagent is done in a manner such that the outer brim 42 at the bottom of the reagent mixing container 10 remains rested on a base 51 of a support unit 55. The base 51 permits the plunger 18 to stay rested, i.e., undisturbed during lyophilization of the liquid as well as during the sealing of the container 10 once the liquid is lyophilized. The base 51 also prevents diluents, if present in the supplemental chamber 14, to remain undisturbed.

Thus, in an embodiment of the invention, during or after lyophilization of the liquid reagent in the reagent mixing container 10, the liquid reagent or the lyophilized version of the liquid reagent remains separated from the contents, such as a diluent or a concentrate that is placed in the lumen 28 of the supplemental chamber 14. Upon sealing, the lyophilized powder is stored without loss of activity or evaporation until mixing of the lyophilized powder with a diluent is desired.

The advantages of the invention are that the reagent preparation, i.e., lyophilization of a liquid reagent in the first chamber 12, and the reconstitution of the lyophilized component with a dilution solution, such as a diluent stored in the supplemental chamber 14, and mixing of the two reagent components can be accomplished automatically in a clinical analyzer without manual intervention, thereby eliminating the possibility of erroneous reagent preparation due to human error, inadvertent contamination of an operator while mixing reagents manually, or inadvertent loss of reagents. In addition, because the volume of each reagent components is defined by the size of the chambers 12 and 14 in the container 10, the ratio at which the two components can be mixed can be controlled.

EXEMPLIFICATIONS

An Exemplary Dual Chamber Reagent Mixing Container for Hemostasis Testing in an Automated Clinical Hemostasis Analyzer Instrument A specific non-limiting example of the dual chamber reagent mixing container according to the invention is a reagent container for prothrombin time (PT) testing by a clinical hemostasis analyzer instrument. The reagent for PT testing contains two components: a diluent and a concentrated PT reagent. The volume ratio between the diluent and the PT reagent is 19:1. Each PT test requires 100 µl diluted PT reagent. A container useful for PT tests in an automated clinical analyzer would require between 500 to 1000 PT tests. A 1000 PT test container requires 100 ml of diluted PT reagent, namely 95 ml diluent and 5 ml concentrated PT reagent. In the exemplary container shown in FIG. 1, the first chamber 12 would have a volume capacity greater than 100 ml and initially contains 95 ml of diluent. The supplemental 14 chamber contains 5 ml concentrated PT reagent. Upon actuation by the plunger 18, the 5 ml of concentrated PT reagent is moved into the lumen 26 of the first chamber 72 following disruption or loss of integrity of the stopper 16. Actuators for moving the plunger 18 are integrated into the hemostasis analytical instrument. An exemplary actuator 32 is illustrated in FIGS. 5A-5C, a stepper motor 34 is used to drive the plunger 18, and an electro-magnetic coil 36 is used to drive the rotation of the magnetic bar-stopper 16 combination or at least one magnetic bead. A self-contained PT reagent mixing container 10 with automated reagent preparation, sustainable for 1000 PT assays, is achieved.

An Exemplary Dual Chamber Reagent Mixing Container for Analyte Testing in an Automated Clinical Analyzer A second non-limiting example of the dual chamber reagent mixing container according to the invention is a reagent container for latex reagent of D-Dimer testing. The latex reagent for D-Dimer is prepared by diluting a concentrated latex reagent (Instrumentation Laboratory Company) with deionized water in a 1:1 volume ratio of concentrated latex reagent:deionized water. Each D-dimer test requires 100 µl of diluted D-dimer latex reagent. A container for 1000 tests requires 100 ml diluted-dimer latex reagent. Therefore, in this exemplary container according to the invention, illustrated in FIG. 1, the first chamber 12 would have a volume capacity larger than 100 ml and initially contains 50 ml of deionized water, and the supplemental chamber 14 contains 50 ml concentrated D-dimer latex reagent. Upon actuation by the plunger 18, the 50 ml of concentrated D-dimer latex reagent moves into the lumen of the first chamber 12 following disruption or loss of integrity of the stopper 16. Actuators for moving the plunger 18 are integrated into the analytical instrument. An exemplary actuator 32 is illustrated in FIGS. 5A-5C, a stepper motor 34 is used to drive the plunger 18, and an electro-magnetic coil 36 is used to drive the rotation of the magnetic bar/stopper 16 combination or at least one magnetic bead. A self-contained D-dimer reagent mixing container 10 with automated reagent preparation, sustainable for 1000 D-dimer assays, is achieved.

We claim:

1. A reagent mixing container, comprising:
   (a) a first chamber having a first end, a second end, and a lumen extending therebetween;
   (b) a supplemental chamber having a first end, a second end, and a lumen therebetween, wherein said second end of said first chamber and said second end of said supplemental chamber are adjacent;
   (c) a stopper enclosing a magnetic bar, the stopper comprising a first position and a second position, wherein in said first position said stopper is positioned to seal the lumen of said first chamber at said second end of said first chamber and the lumen of said supplemental chamber at said second end of said supplemental chamber, and in said second position, said stopper is displaced or compromised from said first position, whereby the lumen of said supplemental chamber is co-extensive with the lumen of said first chamber; and,
   (d) a plunger sealingly positioned at the first end of said supplemental chamber, and slideably moveable in the lumen of said supplemental chamber from the supplemental chamber first end towards said supplemental chamber second end.

2. The reagent mixing container of claim 1 further comprising a reagent component in one of the first chamber and the supplemental chamber.

3. The reagent mixing container of claim 2 wherein said reagent component in one of the first chamber and the supplemental chamber comprises a powder.

4. The reagent mixing container of claim 1 wherein said stopper is elastomeric.

5. The reagent mixing container of claim 1 wherein said stopper encloses at least one magnetic bead.

6. The reagent mixing container of claim 1 wherein said stopper is friction fit between said second end of said first chamber and said second end of said supplemental chamber.

7. The reagent mixing container of claim 1 wherein said stopper is self-lubricating.

8. The reagent mixing container of claim 6 wherein said stopper encloses a magnetic bar.

9. The reagent mixing container of claim 1 wherein said stopper comprises a one-way valve.

10. The reagent mixing container of claim 1 wherein one of said first chamber or said supplemental chamber encloses magnetic particles.

11. A system for automated mixing of reagents, comprising:
   a) a reagent mixing container comprising,
      (i) a first chamber comprising a first end, a second end, and a lumen extending therebetween,
      (ii) a supplemental chamber comprising a first end, a second end, and a lumen therebetween, wherein said second end of said first chamber and said second end of said supplemental chamber are adjacent,
      (iii) a stopper comprising a first position and a second position, wherein in said first position said stopper is positioned to seal the lumen of said first chamber at said second end of said first chamber and the lumen of said supplemental chamber at said second end of said supplemental chamber, and in said second position, said stopper is displaced or compromised from said first position, whereby the lumen of said supplemental chamber is co-extensive with the lumen of said first chamber, and,
      (iv) a plunger sealingly positioned at the first end of said supplemental chamber, and slideably moveable in the lumen of said supplemental chamber from the supplemental chamber first end towards said supplemental chamber second end;
  b) an actuator for slideably moving the plunger into the lumen of the supplemental chamber;
  c) a stepper motor for driving the actuator; and
  d) an electro-magnetic coil for driving rotation of the reagent mixing container.

12. The reagent mixing container of claim 2 wherein said reagent component comprises a concentrated PT reagent.

13. The reagent mixing container of claim 2 wherein said reagent component comprises a concentrated latex D-Dimer reagent.

14. The reagent mixing container of claim 2 wherein said reagent comprises a buffer or water.

* * * * *